(12) United States Patent
Escalier et al.

(10) Patent No.: US 12,096,984 B2
(45) Date of Patent: *Sep. 24, 2024

(54) METHOD AND DEVICE FOR DETERMINING A REFRACTION FEATURE OF AN EYE OF A SUBJECT

(71) Applicant: ESSILOR INTERNATIONAL, Charenton-le-Pont (FR)

(72) Inventors: Guilhem Escalier, Charenton-le-Pont (FR); Konogan Baranton, Charenton-le-Pont (FR)

(73) Assignee: Essilor International, Charenton-le-pont (FR)

( * ) Notice: Subject to any disclaimer, the term of this patent is extended or adjusted under 35 U.S.C. 154(b) by 646 days.

This patent is subject to a terminal disclaimer.

(21) Appl. No.: 17/416,931

(22) PCT Filed: Dec. 19, 2019

(86) PCT No.: PCT/EP2019/086487
§ 371 (c)(1),
(2) Date: Jun. 21, 2021

(87) PCT Pub. No.: WO2020/127849
PCT Pub. Date: Jun. 25, 2020

(65) Prior Publication Data
US 2022/0039649 A1    Feb. 10, 2022

(30) Foreign Application Priority Data

Dec. 20, 2018 (EP) .................................... 18306773

(51) Int. Cl.
*A61B 3/103* (2006.01)
*A61B 3/00* (2006.01)
*A61B 3/14* (2006.01)

(52) U.S. Cl.
CPC ............ *A61B 3/103* (2013.01); *A61B 3/0008* (2013.01); *A61B 3/14* (2013.01)

(58) Field of Classification Search
CPC ......... A61B 3/103; A61B 3/0008; A61B 3/14; A61B 3/12
(Continued)

(56) References Cited

U.S. PATENT DOCUMENTS 5,889,577 A    3/1999 Kohayakawa
6,309,068 B1   10/2001 Kohayakawa
(Continued)

FOREIGN PATENT DOCUMENTS

CN    1742224 A     3/2006
CN    101099164 A   1/2008
(Continued)

OTHER PUBLICATIONS

International Search Report for PCT/EP2019/086487 dated Mar. 11, 2020, 3 pages.
(Continued)

*Primary Examiner* — Mohammed A Hasan
(74) *Attorney, Agent, or Firm* — NIXON & VANDERHYE

(57) ABSTRACT

Disclosed is a method including the steps of: a) illuminating a pupil of the eye of a subject by a light source; b) acquiring at least one picture of the pupil including an image of the reflection of the light source on the retina of the eye, by means of an image-capture apparatus; and c) and determining a refraction feature of the eye from at least a geometrical feature, a positional feature, or an intensity distribution of the image of the reflection of the light source. Optical distances between the pupil and, respectively, the light source and the image-capture apparatus, are different. An associated device is also described.

20 Claims, 5 Drawing Sheets

(58) Field of Classification Search
USPC .................................................. 351/206
See application file for complete search history.

(56) References Cited

U.S. PATENT DOCUMENTS

| | | | |
|---|---|---|---|
| 9,891,445 B1* | 2/2018 | Miller | ............... G02B 27/646 |
| 2003/0025877 A1 | 2/2003 | Yancey | |
| 2006/0044509 A1 | 3/2006 | Fluegge | |
| 2008/0304012 A1 | 12/2008 | Kwon | |
| 2012/0274902 A1 | 11/2012 | Baranton | |
| 2013/0235346 A1 | 9/2013 | Huang | |
| 2015/0374224 A1 | 12/2015 | Baranton | |
| 2015/0374233 A1 | 12/2015 | Zhang | |
| 2016/0143524 A1* | 5/2016 | Bérard | ............... A61B 3/103 351/246 |
| 2019/0206093 A1* | 7/2019 | Chen | ............... G06T 11/00 |
| 2022/0015625 A1* | 1/2022 | Marin | ............... A61B 3/0025 |

FOREIGN PATENT DOCUMENTS

| | | | | |
|---|---|---|---|---|
| CN | 104427924 A | 3/2015 | | |
| CN | 107249431 A | 10/2017 | | |
| EP | 1588209 A1 * | 10/2005 | ............... | A61B 3/11 |
| JP | H05199996 A | 8/1993 | | |
| JP | 11-47094 | 2/1999 | | |
| JP | 4664285 | 4/2011 | | |
| WO | WO-2013036629 A2 * | 3/2013 | ............... | A61B 3/10 |
| WO | 2017/005608 | 1/2017 | | |

OTHER PUBLICATIONS

Written Opinion of the ISA for PCT/EP2019/086487 dated Mar. 11, 2020, 7 pages.
Office Action, issued in Chinese Patent Application No. 201980084063.0 dated Nov. 28, 2023.
Office Action, issued in India Patent Application No. 202117029139 dated Dec. 26, 2022.
Bobier et al., "Eccentric Photorefraction: Optical Analysis and Empirical Measures", American Journal of Optometry & Physiological Optics, Sep. 1985, vol. 62, No. 9, pp. 614-620.
Roorda et al., "Slope-based eccentric photorefraction: theoretical analysis of different light source configurations and effects of ocular aberrations", Journal of the Optical Society of America A, Oct. 1997, vol. 14, No. 10, pp. 2547-2556.
Wesemann et al., "Theory of eccentric photorefraction (photoretinoscopy): astigmatic eyes", Journal of the Optical Society of America A, Dec. 1991, vol. 8, No. 12, pp. 2038-2047.

* cited by examiner

METHOD AND DEVICE FOR DETERMINING A REFRACTION FEATURE OF AN EYE OF A SUBJECT

This application is the U.S. national phase of International Application No. PCT/EP2019/086487 filed Dec. 19, 2019 which designated the U.S. and claims priority to EP Patent Application No. 18306773.5 filed Dec. 20, 2018, the entire contents of each of which are hereby incorporated by reference.

BACKGROUND OF THE INVENTION

Field of the Invention

The invention relates to a method for determining a refraction feature of an eye of a subject.

Description of the Related Art

Numerous documents describe devices and methods for determining such a refraction feature.

In particular, methods of autorefraction are known for determining objective values of the refraction of a subject. These methods are complex and time-consuming. They usually imply the use of large and expensive devices that need a qualified person to be handled.

In particular, they require the use of a specific instrument having a camera and multiple light sources placed in a same plane.

The access to these methods of autorefraction is therefore limited and a large part of the world population does not benefit from them.

SUMMARY OF THE INVENTION

Therefore one object of the invention is to provide a new method for determining a refraction feature of an eye of a subject that would be simplified in that it would not require the use of specific material or the intervention of qualified persons.

The above objects are achieved according to the invention by providing a method for determining a refraction feature of an eye of a subject using a light source and an image-capture apparatus, said method comprising the steps of:
a) illuminating a pupil of the eye of the subject by means of said light source;
b) acquiring at least one picture of said pupil of the eye of the subject comprising an image of the reflection of said light source on the retina of said eye of the subject;
c) determining said refraction feature of said eye of the subject from at least one of the following features of said image of the reflection (31) of said light source (12):
   a geometrical feature (s) of said image of the reflection (31) of said light source,
   a positional feature of said image of the reflection (31) of said light source,
   an intensity distribution within said image of the reflection (31) of said light source;
wherein, said light source and said image-capture apparatus are positioned respectively in an illumination plane and in an image-capture plane that are different from each other, and wherein an absolute value of a difference between:
   an optical distance between said light source and the pupil of the eye of the subject, and
   an optical distance between said image-capture apparatus and said pupil is higher than 0.2 meter.

Such a method does not require the use of the specific device known from the state of the art and described above.

Advantageously, said light source and image-capture apparatus belonging to a portable electronic device and being oriented in opposite directions, and, in step b), the subject faces a mirror and the portable electronic device is placed between said subject and said mirror, in such a way that said picture of the pupil of the eye of the subject is:
   a picture of the eye of the subject acquired without reflection on said mirror, while said pupil is illuminated by a reflection of the light source in the mirror; or
   a picture of a reflection of the eye of the subject in the mirror, while said pupil is illuminated directly by the light source.

Such a method may be implemented by the subject himself, and carried on using a smartphone or a tablet. It is therefore accessible to a wide range of population including some that are excluded from the access to existing methods.

Optional, non-limiting features of the method for virtually testing are disclosed and claimed.

The above mentioned object is also achieved according to the invention by providing a device, also disclosed and claimed. The optional features of the method mentioned above can also be applied to this device.

The description which follows with reference to the appended drawings, which are given by way of non-limiting examples, will make it easy to understand the essence of the invention and how it can be achieved.

DESCRIPTION OF THE PREFERRED EMBODIMENTS

Figure 1:
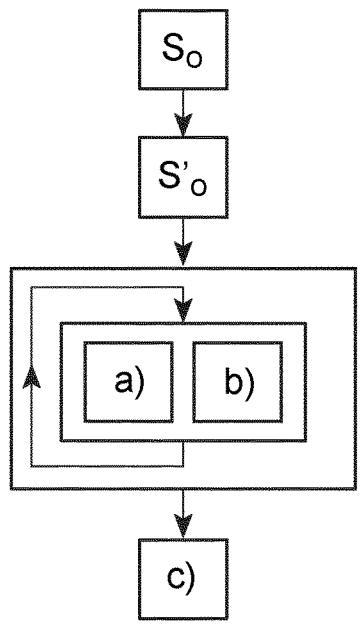
FIG. 1 is a schematic representation of the mains steps of a method, according to the invention, for determining a refraction feature of an eye of a subject.

FIG. 1 represents the main steps of a method, which, by means of eccentric photorefraction, enables to determine a refraction feature of an eye 3 of a subject 2 (FIGS. 2 to 8), such as a spherical power of a refractive error of this eye.

Figure 2:
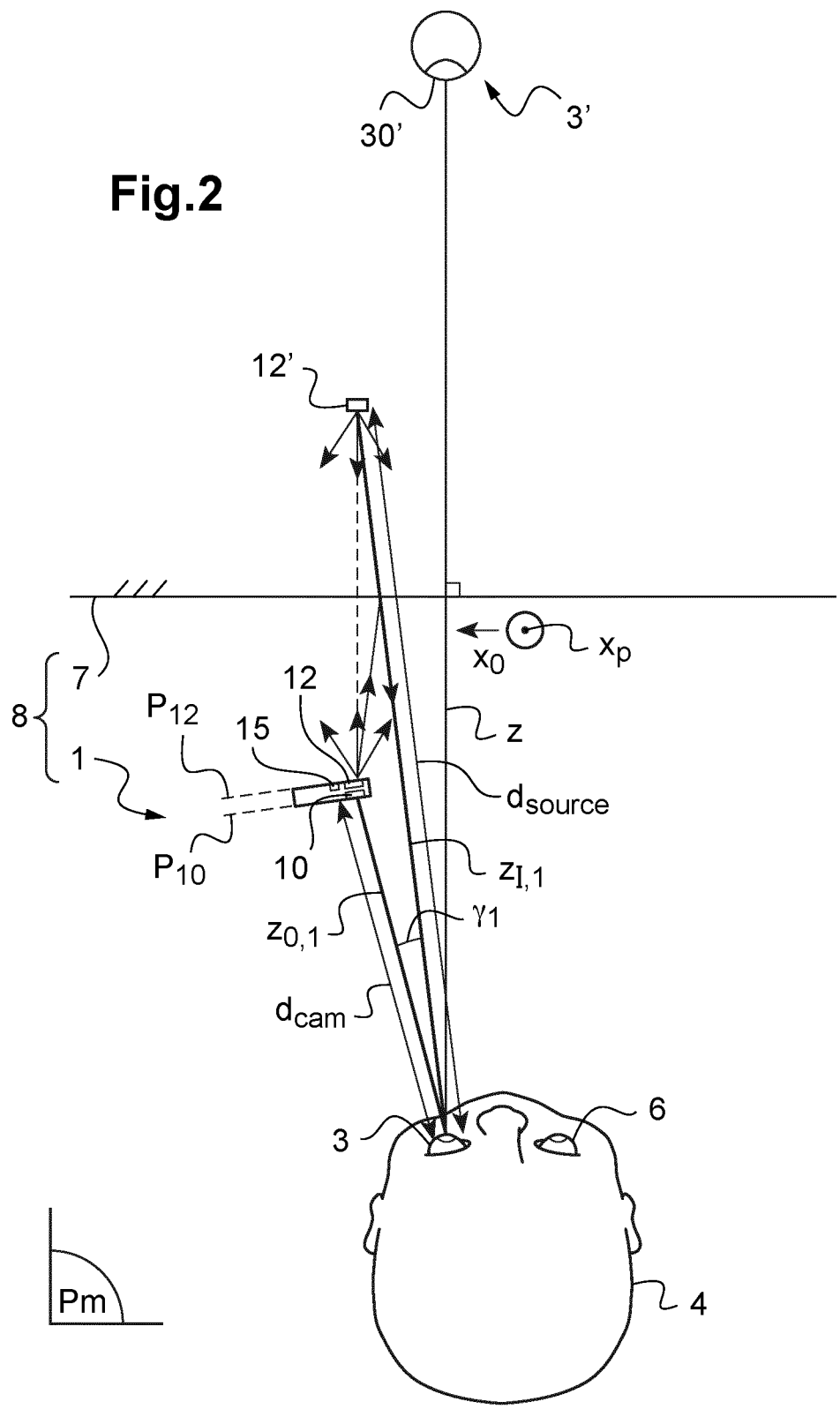
FIG. 2 is a schematic representation, from above, of a first configuration in which a device determines a refraction feature of the eye of the subject, according to the method of FIG. 1.
Figure 8:
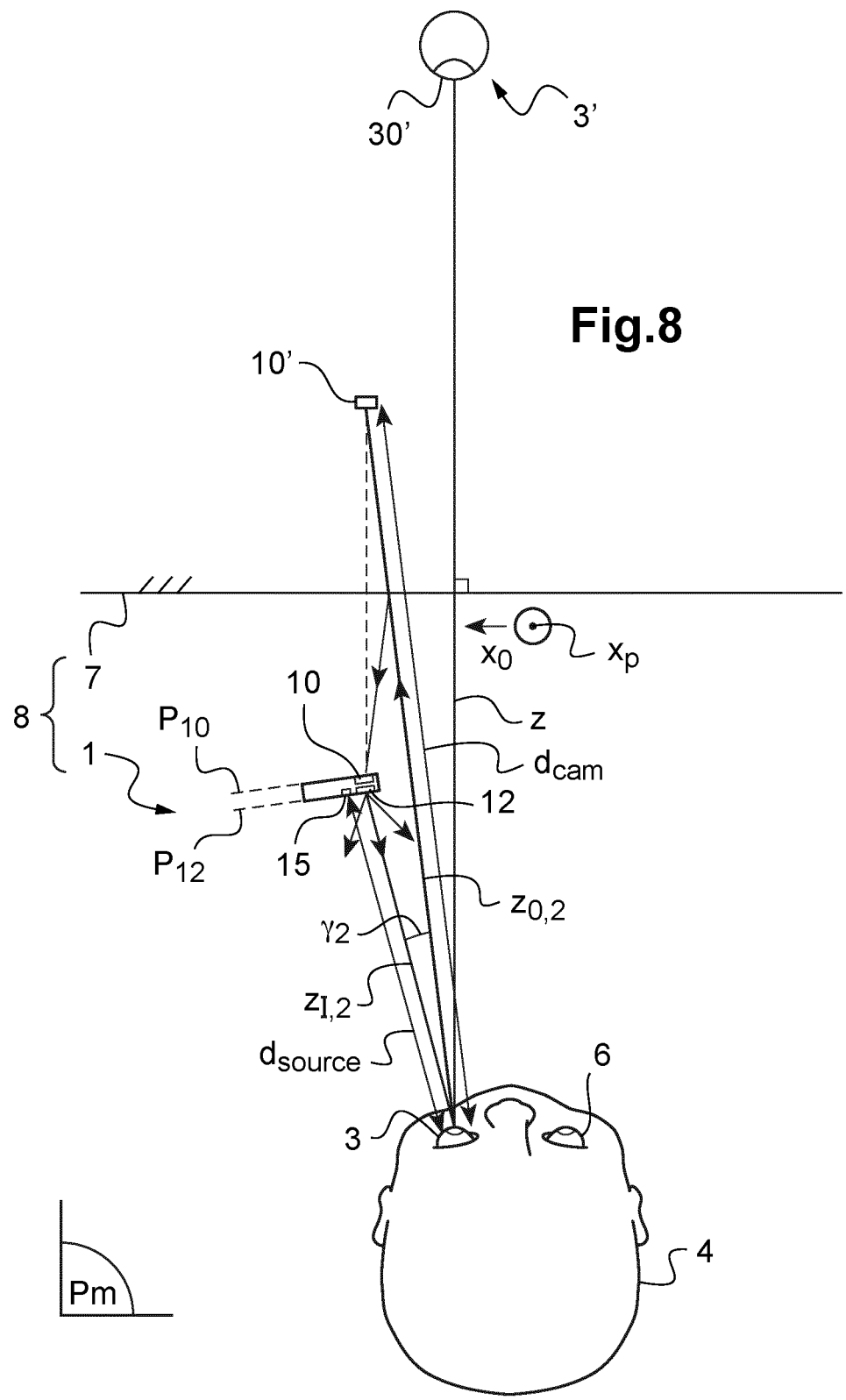
FIG. 8 is a schematic representation, from above, of a second configuration in which a device determines a refraction feature of the eye of the subject, according to the method of FIG. 1.

This method comprises the steps of:

a) illuminating a pupil 30 of the eye 3 of the subject 2 by means of a light source 12 (FIGS. 2 and 8);

b) acquiring at least one picture of said pupil 30 of the eye 3 of the subject comprising an image of the reflection 31 of said light source 12 on the retina of said eye of the subject (FIG. 4), by means of an image-capture apparatus 10;

c) determining said refraction feature of said eye 3 of the subject from at least one of the following features of said image of the reflection 31 of said light source 12:
- a geometrical feature, such as a size s, of said image of the reflection 31 of said light source,
- a positional feature, such as an orientation, of said image of the reflection 31 of said light source,
- an intensity distribution within said image of the reflection 31 of said light source, such as an intensity profile of said image.

In the exemplary embodiments described here, in step c), said refraction feature of said eye 3 of the subject is determined more specifically by taking into account at least one of the following features of said image of the reflection 31 of said light source 12:
- a size s of said image of the reflection 31 of said light source,
- an orientation of said image of the reflection 31 of said light source,
- an intensity profile of said image of the reflection 31 of said light source.

Noticeably, said light source 12 and said image-capture apparatus 10 are positioned respectively in an illumination plane $P_{12}$ and in an image-capture plane $P_{10}$ are different from each other, and spaced apart. An optical distance $d_{source}$ between said light source 12 and the pupil 30 of the eye of the subject is different from an optical distance $d_{cam}$ between said image-capture apparatus 10 and said pupil 30.

The image-capture plane $P_{10}$ is perpendicular, or at least approximately perpendicular to an optical axis of the image-capture apparatus 10, on which the field of view of this apparatus is centered. The illumination plane $P_{12}$ is perpendicular, or at least approximately perpendicular to an average emission direction of the light emitted by the light source 12.

The optical distance $d_{source}$ between the light source 12 and the pupil 30 of the eye of the subject is the length of the average optical path followed by the light, emitted by the light-source 12, that reaches the pupil 30 of the eye 3 of the subject.

The optical distance $d_{cam}$ between the image-capture apparatus 10 and the pupil 30 of the eye of the subject is the length of the average optical path followed by light between the pupil 30 of the eye of the subject and the image-capture apparatus 10.

In the examples describes below with reference to the drawings, an absolute value of the difference between these two optical distances $d_{source}$ and $d_{cam}$ is higher than 0.2 meter.

Having the light source 12 and the image-capture apparatus 10 positioned in different planes, at optical distances from the eye of the subject that different, provides a lot of flexibility.

Indeed, this feature allows for instance to implement the method by using:
- a mirror 7, and
- a portable electronic device 1, like a mobile phone or a tablet computer, that comprises said light-source 12 and said image-capture apparatus 10, instead of using a dedicated professional all-in-one reflectometry apparatus, which is expensive and not accessible to large part of the world population. A first and a second configuration according to this arrangement will be described in more detail below, with reference respectively to FIGS. 2 and 8.

The method according to the invention can also be implemented using two separate, independently mobile apparatuses, like a desk lamp and a mobile phone, to achieve said light-source and said image-capture apparatus (this alternative configuration is not represented in the figures).

In any of these configurations, the refraction feature of the eye 3 of the subject 2 is thus determined by eccentric photorefraction, by means of very general-purpose and widely-spread devices like said portable electronic device 1.

Below, a device for implementing the method, and the first and second exemplary configurations mentioned above will be described first.

Then, the principle of eccentric photorefraction and the way it is adapted to these configurations will be presented.

And then, the different steps of the method will be described in more detail.

Device for Implementing the Method

In these first and second configurations, the method is implemented using a device 8 that comprises the above-mentioned mirror 7 and portable electronic device 1, the subject 2 facing the mirror 7 while the portable electronic device 1 is placed between the subject 2 and the mirror 7 (FIGS. 2 and 8).

The mirror 7 is a flat mirror.

The portable electronic device 1, here a smartphone or a tablet computer, has the shape of a flat and thin slab extending between a front face 13 and a back face 14.

The light source 12 and the image-capture apparatus 10 are, for example, located respectively on the front face 13 and on the back face 14 of the portable electronic device 1, and are oriented in opposite directions.

In other words, the field of view of the image-capture apparatus 10 extends, from the image-capture apparatus 10, in a direction opposite to the emission direction of the light emitted by the light source 12. The light emitted by the light source 12 is forwardly-directed with respect to the portable electronic device 1 while the field of view of the image-capture apparatus 10 is backwardly-directed.

In these first and second configurations, the illumination plane $P_{12}$ and the image-capture plane $P_{10}$ coincide respectively with the front face 13 and with the back face 14 of the portable electronic device 1.

The image capture apparatus 10 is a small, general purpose digital camera. Here, its entrance pupil 100 is located in the vicinity of an entrance face of a front lens of the image-capture apparatus 10 (FIG. 6), and has a diameter close to the diameter of said entrance face.

Optionally, the portable electronic device 1 comprises an additional image-capture apparatus 15 and/or a screen 11.

The additional image-capture apparatus 15 is also a small, general purpose digital camera. It is located on the same, front face 13 as the light source 12 and is oriented in the same direction as the light emitted by that source. Its field of view is thus forward-directed with respect to the portable electronic device 1.

The screen 11, for instance a back-lighted LCD screen ("Liquid Crystal Display" screen), lies either on the back, or on the front face of the portable electronic device.

The light source 12 may comprise one or several LEDs ("Light Emitting Diodes") or a small electrical arc lamp. In the exemplary embodiments described here, the light source 12 is distinct from the screen 11 and is a lamp that can provide additional lighting when shooting pictures, or when the portable electronic device 1 is used, occasionally, as an adjunct portable lamp. Alternatively, the light source could be a lighted area displayed on a screen of the portable electronic device (this variant is not represented in the figures).

Here, the portable electronic device 1 comprises an optional communication module (not represented in the figures), that enables to exchange data between the portable electronic device 1 and a remote computer or server through a communication network like the internet.

The portable electronic device 1 comprises also a control unit (not represented on the figures), comprising at least a processor and a memory.

Remarkably, except from the dedicated computer program (a computer application, sometimes called "applet") stored in said memory, whose execution by the processor causes to execute the steps of the above-mentioned method, the portable electronic device 1 has no additional features or components, compared to a standard, general purpose, stand-alone smartphone or tablet computer designed mainly for communication (that is to telephone, to participate to a videoconference or to access webpages).

First and Second Configurations

Figure 3:
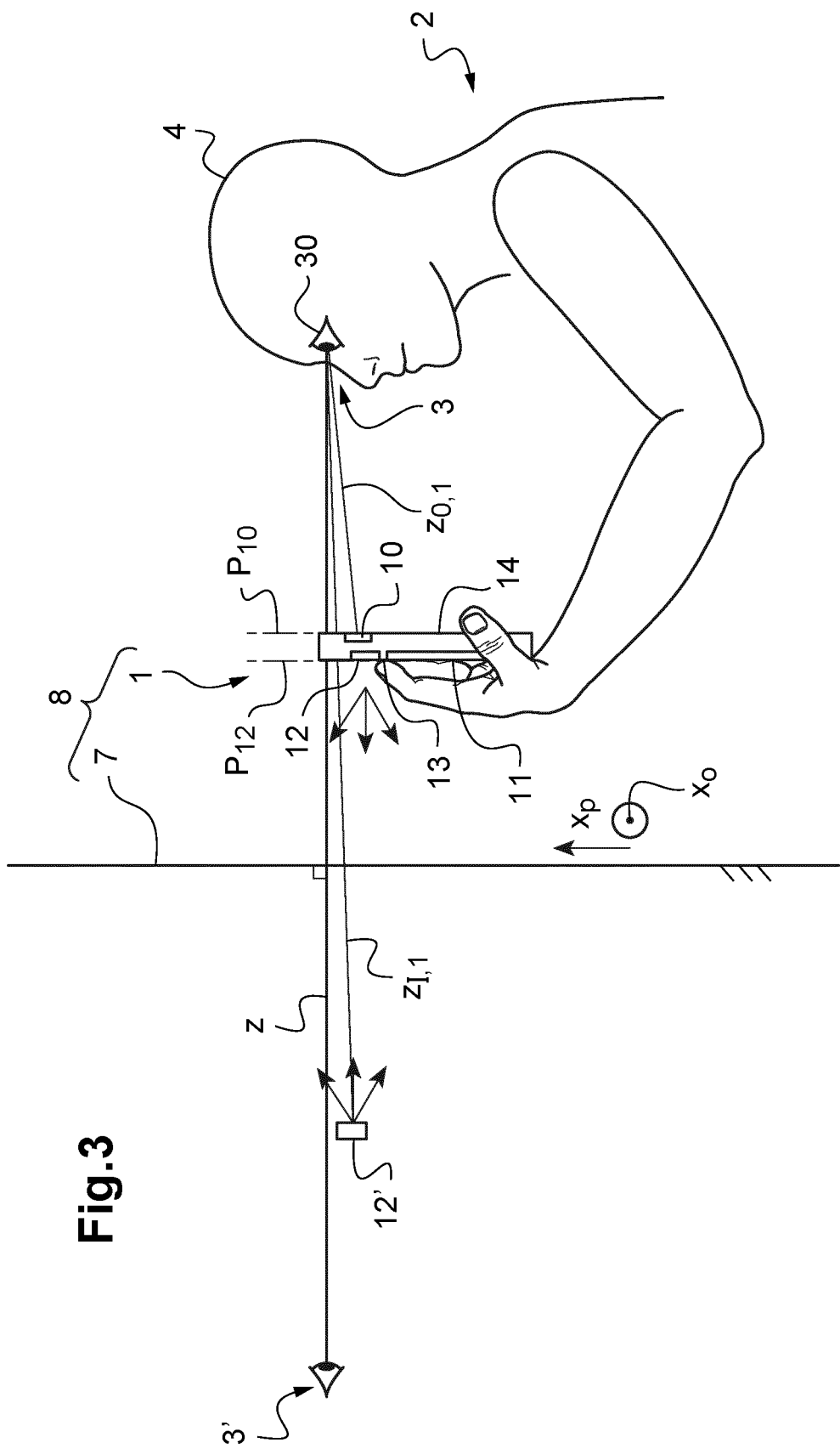
FIG. 3 is a schematic representation of the configuration of FIG. 2, with a view from the side.

In the first configuration, the portable electronic device 1 is oriented so that, in step b), the picture of the pupil 30 of the eye of the subject is acquired without reflection on the mirror 7, while this pupil 30 is illuminated by a reflection 12' of the light source 12 in the mirror 7 (FIGS. 2 and 3).

So, the light source is oriented towards the mirror 7, while the field of view of the image-capture apparatus 10 is directed in the opposite direction, towards the subject 2.

In this first configuration, the reflection 31 on the retina of the eye 3 of the subject, of the light emitted by the light source 12, is collected directly by the image-capture apparatus 10, without having been reflected by the mirror 7. More generally, it is collected without having interacted with any optical component, apart from, optionally, a corrective ophthalmic lens or a contact lens worn by the subject 2.

On the contrary, the light, emitted by the light source 12, that illuminates the pupil 30 of the eye 3, is reflected by the mirror 7 before reaching this pupil 30.

In the second configuration, the portable electronic device 1 is oriented so that, in step b), the picture acquired by the image-capture apparatus 10 is a picture of a reflection 3' of the eye 3 of the subject in the mirror, while said pupil 30 is illuminated directly by the light source (FIG. 8).

So, the field of view of the image-capture apparatus 10 is directed towards the subject 2, and the light source 12 is oriented in the opposite direction, towards the mirror 7.

In this second configuration, the light emitted by the light source 12 reaches the pupil 30 of the eye 3 of the subject without being reflected by the mirror 7. More generally, it reaches the pupil 30 without having interacted with any optical component, apart from, optionally, a corrective ophthalmic lens or a contact lens worn par the subject 2.

On the contrary, the reflection 31 on the retina of the eye 3 of the subject, of the light emitted by the light source 12, is first reflected by the mirror 7, and then collected by the image-capture apparatus 10.

Both in this first and in this second configuration, the pupil of eye of the subject is thus illuminated, directly, by an effective light source 12', 12, which:

in the first configuration, is a virtual light source corresponding to the reflection 12' of the light source 12 in the mirror 7, and which in the second configuration, is the light source 12 itself.

Regarding said retinal reflection 31, it is collected directly, without reflection on a mirror, by an apparent image-capture apparatus 10, 10', which:

in the first configuration, is the image-capture apparatus itself, and which in the second configuration, is a virtual image-capture apparatus corresponding to the reflection 10' of the image capture apparatus 10 in the mirror 7.

The light rays corresponding to the retinal reflection 31 go directly from the retina of the eye of the subject to the apparent image-capture apparatus 10, 10', without being reflected by a mirror.

Having the light source 12 and the image-capture apparatus 10 oriented in opposite directions, and illuminating or visualizing the pupil 30 of the eye of the subject through a reflection on the mirror 7, allows varying easily:

a first side shift, between the reflection 12' of the light source in the mirror 7 and the image-capture apparatus 10, or a second side shift, between the light source 12 and the reflection 10' of the image-capture apparatus 10 in the mirror 7, by moving the portable electronic device 1 with respect to the head of the subject.

Remarkably, this is achieved even if the light source 12 and the image-capture apparatus 10 are solidary, embedded in the same portable electronic device. Varying this first or second side shift enables to improve the accuracy of the refractive feature or features of the eye 3 of the subject determined by eccentric photorefraction.

In addition, facing a mirror induces the subject to look at elements, such as his own reflection in the mirror, that are located far away from him from an optical point of view, at a long optical distance from his eye 3. The eye 3 of the subject thus focuses on, that is to say accommodates on, optically distant elements during the acquisition of said picture, at step b), which facilitates the subsequent determination of the refraction feature of this eye.

The plane of the mirror 7 is approximately vertical (FIG. 3).

In these two exemplary configurations, the subject 2 holds the portable electronic device 1 by himself, for instance in one of his hands. The portable electronic device 1 is located approximately at an arm's length from the eye 3 of the subject, at a distance from his eye 3 comprised between 0.2 meter and 1 meter.

As already indicated, the absolute value of the difference between:

the optical distance $d_{source}$ between the light source 12 and the pupil 30 of the eye 3 of the subject, and the optical distance $d_{cam}$ between the image-capture apparatus 10 and said pupil 30 is higher than 0.2 meter.

In these first and second exemplary configurations, this means that a geometrical, actual distance between the portable electronic device 1 and the mirror 7 is higher than 0.1 meter, or at least substantially higher than 0.1 meter.

Having the portable electronic device 1 spaced apart from the mirror 7 from at least 0.1 meter enables to capture pictures of the eye of the subject that correspond to moderate side shifts of the effective light source 12; 12'. Moderate side shifts, which correspond to moderate values of an eccentricity parameter that is described in detail below, are well suited to determine precisely the refractive feature or features of the eye 3 of the subject, in particular when the refractive error of this eye is small.

Placing the portable electronic device very close to the mirror, for instance at 1 centimeter from it, would lead to very high values of the eccentricity parameter that are not appropriate to determine the refractive feature or features of the eye of the subject.

In the embodiments described here, the absolute value of the difference between the optical distances $d_{source}$ and $d_{cam}$ is preferably smaller than 4 meters, or even smaller than 2 meters. When this difference is equal to 2 meters, the portable electronic device 1 is approximately 1 meter away from the mirror 7. Placing the portable electronic device 1 in this way, not to far from the mirror 7, enables to keep both the optical distance $d_{source}$ and the optical $d_{cam}$ rather small, thus enabling both to illuminate the eye 3 of the subject with an intense light, and to acquire the picture of his eye with a high magnification.

So, finally, having the absolute value of said difference comprised between 0.2 meter and 4 meters, or even comprised between 0.2 meter and 2 meters, turns out to be well suited to implement the method described below, leading to a precise and convenient determination of the refractive feature or features of the eye 3 of the subject.

In the alternative configuration not represented in the figures where the method according to the invention is implemented using two separate, independently mobile apparatuses, like a desk lamp and a mobile phone, to achieve said effective light source and said apparent image-capture apparatus, either the independent light source or the independent image-capture apparatus may be moved relative to the eye of the subject in order to vary the distance between apparent image capture apparatus and effective light source. The desk lamp is for example place behind the mobile phone, said mobile phone being placed between the desk lamp and the head of the subject.

Eccentric Photorefraction

In this method, the determination of the refraction feature of the eye 3 of the subject is based on the technique of eccentric photorefraction (a type of retinoscopy technique), as described for instance in the article "Eccentric Photorefraction: Optical Analysis and Empirical Measures" by W. R. Bobier and O. J. Braddick (American Journal of Optometry and Physiological Optics, 1985, vol. 62, No. 9, pp. 614-620).

The refraction features that can be determined using this technique comprise: the spherical power of a refractive error of the eye, a cylindrical power of this refractive error, and an orientation of the axis of the corresponding cylinder.

Figure 4:
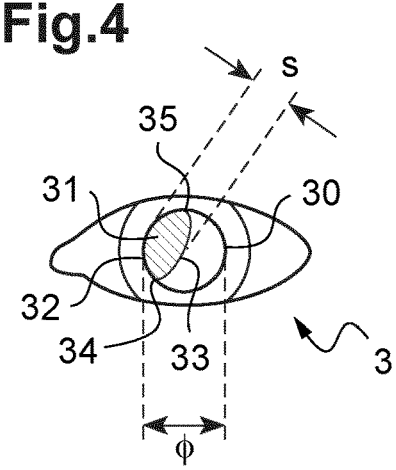
FIG. 4 is a schematic representation of the eye of the subject, as it is visualized by an image-capture apparatus of the device of FIG. 2.

When the eye 3 of the subject is ametropic, in a picture of this eye 3 acquired by the image-capture apparatus 10, an image of the reflection 31, on the retina of the eye 3, of the light source 12, occupies a portion only of the image of the pupil 30 of this eye, this portion being in the shape of a crescent (FIG. 4). More precisely, this retinal reflection 31 is bounded by two curved arcs 32, 33 that intersect each other to form two sharp ends 34, 35 of the crescent.

A size s of the reflection 31 thus detected provides information regarding a value of the ametropia of the eye 3.

Here, the size s of said reflection 31 designates a width of this reflection, in a direction perpendicular to the axis that passes through the two sharp ends 34, 35 of the crescent. The size s is the width of this reflection 31 in real space, in the plane of the pupil 30 of the eye. The size s of the reflection 31, in real space, can be determined from a dimension si of the image of this reflection, expressed as a number of pixels, for instance, measured in the picture of the eye 3 captured by the image-capture apparatus 10. The dimension si of the image of the reflection 31, measured in the picture of the eye 3 captured by the image-capture apparatus 10, can be determined, for instance, as the full width at half-maximum of an intensity peak of an intensity profile of said image.

In the case of the present method, in which the light source and the entrance pupil of the image-capture apparatus are located in different planes, it can be shown by optical ray tracing that the same formulas as in the article by W. R. Bobier and O. J. Braddick can be used to determine the spherical power of a refractive error of this eye 3, provided that the eccentricity introduced in this article is replaced, in said formulas, by the eccentricity parameter e, defined below.

This eccentricity parameter e is representative of a side shift between the effective light source 12', 12 and the apparent image-capture apparatus 10, 10'.

In the case of the first configuration, the eccentricity parameter e is thus representative, more specifically, of the first side shift between the reflection 12' of the light source in the mirror 7 and the image-capture apparatus 10. The value of the eccentricity parameter e is then determined as a first distance e1, in the plane of the entrance pupil 100 of the image-capture apparatus, between (FIG. 6):
- the edge F1, which is the closest to the entrance pupil 100, of the light beam F that is emitted by the light source 12 and that is intercepted by the pupil 30 of the eye of the subject, and
- the edge 101 of the entrance pupil 100, at the extremity of this pupil, that is the closest to this light beam.

In the case of the second configuration, the eccentricity parameter e is representative of the second side shift between the light source 12 and the reflection 10' of the image-capture apparatus in the mirror 7. The value of the eccentricity parameter e is then determined as a second distance e2 between:
- an edge of the geometrical prolongation, backward of the light source, of the light beam that is emitted by the light source 12 and that is intercepted by the pupil 30 of the eye of the subject, and
- the edge of the reflection in the mirror 7 of the entrance pupil of image-capture apparatus, this edge being the closest to said prolongation of said light beam.

A value of the ametropia of the eye 3, equal to a spherical power SP of a refractive error of this eye 3, can then be determined on the basis of:
- the above-mentioned size s of the crescent-like reflection 31, on the retina of the eye, of the light-source 12,
- a diameter $\phi$ of said pupil 30,
- the optical distance $d_{cam}$ between the entrance pupil 100 of the image capture apparatus 10 and the pupil 30 of the eye 3 of the subject 2, and of
- the eccentricity parameter e defined above.

For instance, the spherical power SP can be determined according to the following formula: $(s-\phi)\cdot SP=e/(d_{cam}+1/SP)$.

As the effective light source 12', 12 is shifted aside with respect to the apparent image-capture apparatus 10, 10', the light source 12 and the center O of the entrance pupil 100 of the image-capture apparatus, viewed from said eye 3, are visually located in different directions, angularly separated.

More specifically, in the first configuration (FIGS. 2 and 6):
   a first illumination axis $z_{i1}$, linking the eye 3 of the subject to the reflection 12' of the light source in the mirror 7, and
   a first observation axis $z_{o1}$, linking the eye 3 of the subject to the center O the entrance pupil 100 of the image-capture apparatus
   are separated by a first offset angle $\gamma_1$.
And in the second configuration (FIG. 8):
   a second illumination axis $z_{i2}$, linking the eye 3 of the subject to the light source 12, and
   a second observation axis $z_{o2}$, linking the eye 3 of the subject to the center of the reflection in the mirror 7 of the entrance pupil of image-capture apparatus 10,
   are separated by a second offset angle $\gamma_2$.

Figure 6:
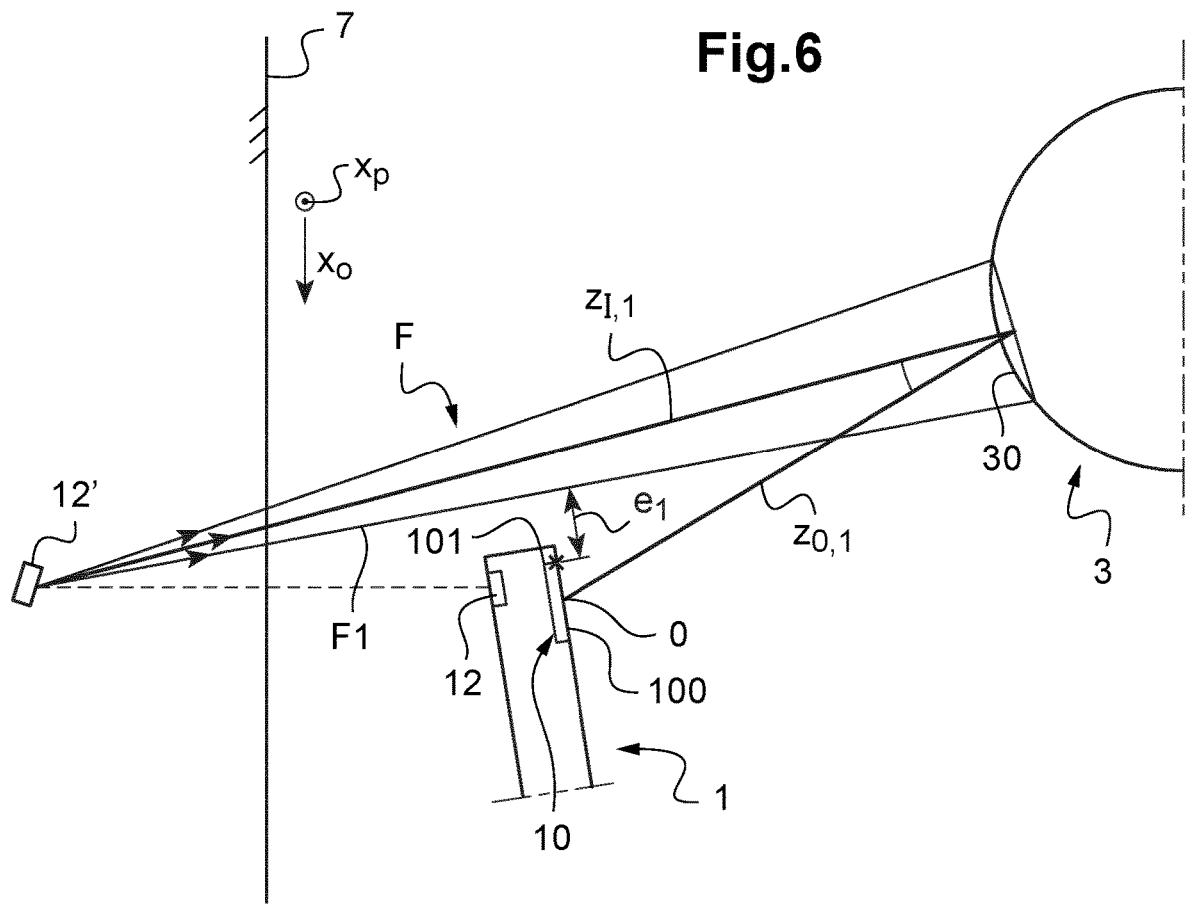
FIG. 6 represents in more details some aspects of the configuration of FIG. 2.

Varying the first or second offset angle $\gamma_1, \gamma_2$ causes the eccentricity parameter e to vary, as can be seen for instance in FIG. 6.

The first observation and illumination axis $z_{o1}$ and $z_{i1}$, or, in the case of the second configuration, the second observation and illumination axis $z_{o2}$ and $z_{i2}$, define a measurement plane Pm, which include either the first observation and illumination axis, or the second observation and illumination axis.

As an example, in the case of FIGS. 2 and 8, the portable electronic device 1 is located so that this measurement plane Pm is approximately horizontal, and parallel to the Frankfurt plane of the head 4 of the subject 2.

It is recalled that the Frankfurt plane of the head of a subject is the plane passing through the inferior margin of its left orbit and the upper margin of each ear canal or external auditory meatus of the subject. The Frankfurt plane is most nearly horizontal when the subject is standing upright, in a relaxed posture, looking straight ahead in the distance.

The orientation of this measurement plane Pm, with respect to the eye 3 of the subject, plays a role in the determination of astigmatism features of the eye 3 of the subject, as explained below.

These astigmatism features, which comprise the cylindrical power of the refraction error of the eye 3, and the orientation of the axis of the corresponding cylinder, can indeed be determined by acquiring several pictures of the eye 3 of the subject 2, for a respective plurality of orientations of the measurement plane Pm.

For instance, these different pictures can be acquired while the measurement plane Pm is successively parallel, perpendicular and then oriented at 45 degrees relative to the Frankfurt plane of the subject 2. When the subject 2 is a relaxed posture, looking at the mirror 7, the measurement plane Pm is then successively horizontal, vertical and then oriented at 45 degrees relative to the vertical.

On the basis of the pictures thus acquired, the size s of the reflection 31 of the light source 12 on the retina of the eye 3 is then determined for each of these orientations of the measurement plane, and hence, for different meridians of the eye 3.

In addition, for each of these orientations, the shape of the crescent-like image of said reflection 31 can be exploited to determine an orientation, that is, an angular position, of this reflection 31 with respect to the measurement plane Pm. This orientation corresponds here to a tilt angle between the axis of said crescent and a direction perpendicular to the measurement plane Pm. The axis of the crescent is the axis that passes through the two sharp ends 34, 35 of the crescent.

The cylindrical power of the refraction error of the eye 3, and the orientation of the axis of the corresponding cylinder can then be determined, from this set of values of the size s and of the tilt angle of the reflection 31, determined for the respective plurality of orientations of the measurement plane Pm. This determination can be achieved as explained in the article "Theory of eccentric photorefraction (photoretinoscopy): astigmatic eye" by W. Wesemann; A. M. Norcia and D. Allen (Journal of the Optical society of America A, December 1991, vol. 8, No. 12, pp. 2038-2047), for instance.

The refraction features of the eye of the subject can also be determined on the basis of an intensity profile of the reflection 31 of the light source on the retina of the eye 3 of the subject, instead of being determined on the basis of the size s of the retinal reflection 31.

This intensity profile of the retinal reflection 31 is a cross section of the intensity of said reflection 31, across a meridian of the pupil 31, for instance across the meridian of the pupil parallel to said measurement plane. In other words, this intensity profile is an ensemble of values representative of the variation of the intensity, that is to say representative of the variation of the luminous power, or of the variation of the luminous power per area, within the reflection 31, as a function of a position across said meridian of the pupil.

The determination of the refraction features of the eye of the subject, from this intensity profile can be achieved according to the following article, for instance: "Slope-based eccentric photorefraction: theoretical analysis of different light source configurations and effects of ocular aberrations" by A. Roorda, M. Campbell and W. Bobier (Journal of the Optical Society of America, A, Vol. 14, No. 10, October 1997, pp 2547-2556).

In the present method, the refraction features of the eye of the subject could also be determined both:
   on the basis of the size/orientation of the retinal reflection 31, and
   on the basis of the intensity profile of the retinal reflection 31.

In this case, the values of the refraction features determined from said size/orientation can, for instance, be averaged with those deduced from the intensity profile to obtain estimations of these refraction features having an improved accuracy/reliability.

In the alternative configuration not represented in the figures where the method according to the invention is implemented using two separate, independently mobile apparatuses, like a desk lamp and a mobile phone, to achieve said effective light-source and said apparent image-capture apparatus, the eccentricity parameter e is representative of the side shift between the light source and the image-capture apparatus.

Detailed Presentation of the Steps of the Method

Apart from some features related to the scaling of the pictures acquired and/or distance conversions, and/or optionally, to the determination of the optical distance $d_{source}$, the refractive features of the eye of the subject are here determined in the same way in the case of the first configuration (FIG. 2), and in the case of the second configuration (FIG. 8) described above.

The method is described below in the case of a determination of the refractive features of the eye based on the size and orientation of the retinal reflection 31. However, these refractive features could also be determined on the basis of one or several intensity profiles of said reflection, as mentioned above.

Prior to steps a) and b), the method comprises here a preliminary calibration step So (FIG. 1).

During this calibration step, the portable electronic device 1 determines the optical distance $d_{cam}$ between the pupil 30 to be illuminated, and the entrance pupil 100 of the image-capture apparatus 10.

This optical distance $d_{cam}$ is determined here by scaling a picture of the subject's face, of the subject's eyes 3, 6 or eye 3 acquired by the image-capture apparatus 10, in position of use between the mirror 7 and the subject 2.

To this end, the subject may be incited, by a message displayed on the screen 11, or by an audible message, to hold a predetermined object, like a credit card, close to his eye. The above-mentioned picture is then acquired by the image-capture apparatus 10. The predetermined object has a known size, for instance a known width, whose value is stored in the memory of the portable electronic device. From the size of that object, measured in the acquired picture (and thus expressed as a number of pixels), the portable electronic device 1 determines the optical distance $d_{cam}$ between the pupil 30 and the entrance pupil 100 of the image-capture apparatus 10. To this end, the portable electronic device 1 may use a calibration curve or look-out table relating the size of such an object, measured in an acquired picture, to said optical distance $d_{cam}$, this calibration curve or look-out table being stored in the memory of the portable electronic device 1.

The determination of the optical distance $d_{cam}$, by scaling a picture of the subject's face, or of the subject's eyes or eye, acquired by the image-capture apparatus 10, could also be carried on by:
- identifying, in said picture, as least two remarkable points of the subject's face, and by
- determining the optical distance $d_{cam}$ from at least a distance (expressed as a number of pixels), in the captured image, between these two remarkable points.

These remarkable points are points of the face that can be easily identified and precisely and located by image analysis. One of these points can be located, for instance, at the medial or lateral commissure, or at the center of the pupil of one of the eyes of the subject.

A reference distance between the two identified remarkable points is stored in the memory of the portable electronic device, and the portable electronic device is configured to:
- compare the distance, in the captured image, between the two identified remarkable points, to this reference distance, and to
- determine the optical distance $d_{cam}$ on the basis of the result of this comparison.

The picture scaling described above is also used to determine a conversion coefficient C, that relates the size of an element of the eye of the subject, in an image captured by the image-capture apparatus 10 (size that is thus expressed as a number of pixels), to the actual size of this element, in real space (expressed for instance in millimeters). This conversion coefficient C is employed, in step c), to determine the diameter $\phi$ of the pupil 30 of the eye 3 and the size s of the retinal reflection 31, from the picture or pictures of eye 3 acquired in step b).

In the example represented in FIG. 1, the calibration step So is executed prior to steps a) and b). However, alternatively, the calibration step So could be executed after steps a) and b), directly on the basis of the picture or pictures acquired in step b).

This method also comprises, prior to the steps a) and b), an optional step for giving measurement instructions to the subject, S'o (FIG. 1).

During this step, the subject 2 is incited, by a message displayed on the screen 11, or by an audible message, to look at a particular point, or in a particular direction.

More precisely, during this step S'o, the subject 2 is incited to direct his gaze towards:
- the entrance pupil 100 of the image-capture apparatus, or
- towards the reflection of the entrance pupil of said image-capture apparatus 10 in the mirror 7 (in the case of the second configuration), or
- towards the light source 12, or
- towards the reflection 12' of the light source 12 in the mirror 7 (in the case of the first configuration), or
- towards the reflection 3' of his eye 3 in the mirror 7, or
- towards his own reflection, for instance the reflection of his own face, in the mirror, or
- towards a visual target, corresponding to an element located far away from his eye 3 from a visual point of view, for instance at more than 5 meters.

Thanks to this message, the subject 2 directs his gaze towards one of these elements during the execution of the method.

During step S'o, the subject is also incited to reduce ambient light intensity as much as possible, and/or to go to a place with low ambient light intensity.

Steps a) and b) are now described in detail.

In step a), the light source 12 preferably illuminates the pupil 30 of the eye by a flash of light, that is by a brief pulse of light, rather than illuminating it continuously. Indeed, a photorefraction measurement is all the more precise than the pupil 30 of the eye 3 is dilated, and with a brief or intermittent illumination of this pupil, contraction/closure of the pupil can be avoided, or at least is smaller than with a continuous illumination. Here, the duration of this flash of light, defined for instance as this pulse of light full temporal width at half-maximum, is smaller than 0.1 second, or even smaller than 0.03 seconds. If the emission of this flash of light is periodically repeated with a given period, the ratio of this flash duration to said period is smaller than 10 percent (10%).

The image-capture apparatus 10 and the light source 12 operations are synchronized, so that the picture acquired at step b) is acquired while the pupil 30 of the eye is being illuminated by this flash of light.

The group of steps comprising step a) and step b) can be executed one time only. However, in the exemplary embodiment of the method described here, this group of steps is executed several times successively (as represented on FIG. 1) in order:
- to acquire a plurality of pictures of the eye, for a respective plurality of values of the eccentricity parameter e, and/or
- to acquire a plurality of pictures of the eye, for a respective plurality of orientations of the measurement plane Pm, so that astigmatism features of the eye 3 can be determined.

To this end, the group of steps comprising step a) and step b) is executed several times successively for a respective plurality of postures of the head 4 of the subject relative to the light source 12 or to the reflection 12' of the light source in the mirror.

The posture of the head 4 of the subject relative to the light source 12 comprises a relative position and/or a relative orientation of the head and light source.

In other words, the group of steps comprising step a) and step b) is executed several times successively for a respective plurality of positions and/or orientations of the head 4 of the subject 2, relative to the light source 12 or relative to the reflection 12' of the light source in the mirror 7.

So, for instance, during these successive executions, the portable electronic device 1 is be held stationary while the subject 2 rotates his head 4 or moves it in a translational motion.

The subject 2 may also hold his head 4 stationary while the portable electronic device 1 is moved, for instance in a translational motion parallel to the mirror 7.

More specifically, the relative motion of the head 4, and thus of the eye 3 of the subject, with respect to the light source 12, is carried on so that the light source 12 is shifted from, that is to say spaced from, a reference axis z that links the pupil 30 of the eye 3 and its reflection 30' in the mirror 7. Varying thus the lateral offset of the light source 12 with respect to this reference axis z causes the first or the second offset angle $\gamma_1$, $\gamma_2$ to vary (see FIGS. 2 and 7), and, so, causes the eccentricity parameter e to vary.

An appropriate motion of the light source 12 with respect to the reference axis z, which is done here by moving the portable electronic device 1, enables also to vary the orientation of the measurement plane Pm. For instance, when the portable electronic device 1 is placed on the left (or right) of this axis, at the same height as the eye 3 of the subject, the measurement plane is approximately horizontal, while when the portable electronic device 1 is placed along the vertical, below that axis, the measurement plane is approximately vertical.

The method comprises here three sets of successive executions of the illumination and acquisition steps a) and b). During these sets of executions, the subject 2 stands upright, in front of the mirror.

Figure 7:
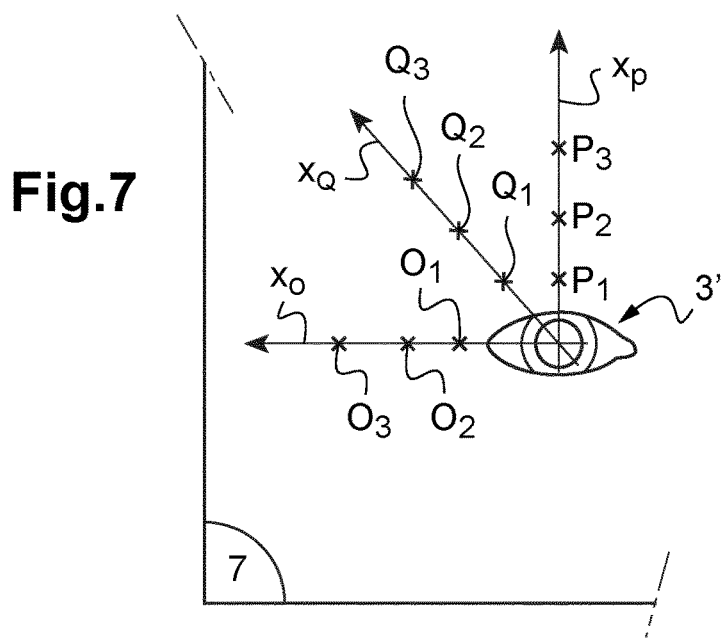
FIG. 7 represents schematically various sets of positions, on which a light source is successively centered during the method of FIG. 1.

During a first set of these successive executions, the portable electronic device is moved, from one execution to the other, in parallel to the mirror, so that the light source 12 is centered successively on a respective plurality of distinct positions O1, O2, O3, . . . , as represented on FIG. 7. These positions O1, O2, O3, . . . , are located along an first axis $x_O$, parallel to the mirror 7. Here, the first axis $x_O$ is horizontal, and parallel to the Frankfurt plane of the head 4 of the subject 2. The O1, O2, O3 are located respectively at different offset distances from the reference axis z.

During a second set of successive executions of the group of steps comprising steps a) and b), the portable electronic device is moved similarly as during the first set, except that the positions P1, P2, P3, . . . , on which the light source 12 is successively centered during this second set, are located along a second axis $x_P$, parallel to the mirror 7 and perpendicular to the first axis $x_O$ (FIG. 8).

During a third set of successive executions of the group of steps comprising steps a) and b), the portable electronic device is moved similarly as during the first set, except that the positions Q1, Q2, Q3, . . . , on which the light source 12 is successively centered during this third set, are located along a third axis $x_Q$, parallel to the mirror 7 and tilted with respect to the first and second axis axis $x_O$ and $x_P$, for instance at 45 degrees relative to these axis (FIG. 8).

During each of these sets of executions, the orientation of the measurement plane Pm is approximately constant, while the eccentricity parameter varies. And from one set to the other, the orientation of the measurement plane changes, this plane being successively horizontal, vertical, and tilted between the vertical and the horizontal.

In a variant, during these three sets of measurements, the portable electronic device could be held stationary, while the subject rotates his head. In this case, during the first set, the subject would rotate his head from right to left, around his craniocaudal axis, that is around an axis perpendicular to its Frankfurt plane, this axis being vertical, here. This rotation causes his eye, and so the reference axis z, to move relative to the light source, thus causes the eccentricity parameter to vary. And during the second set, the subject would for instance rotate his head top-down, around an axis perpendicular to its sagittal plane.

Prior to and/or during the successive executions of steps a) and b) described above, the subject 2 is instructed to move his head 4 and/or to move the portable electronic device 1 as explained above, by a message displayed on the screen 11 or by an audible message emitted by the portable electronic device 1.

It is noted that, during these successive executions of steps a) and b), the head 4 of the subject is moved relative to the light source 12 while the optical distance $d_{cam}$ between the image-capture apparatus 10 and the pupil 30 of the eye remains constant. Keeping the optical distance $d_{cam}$ constant prevents from having to determine again this distance, that has been previously determined at step So.

Figure 5:
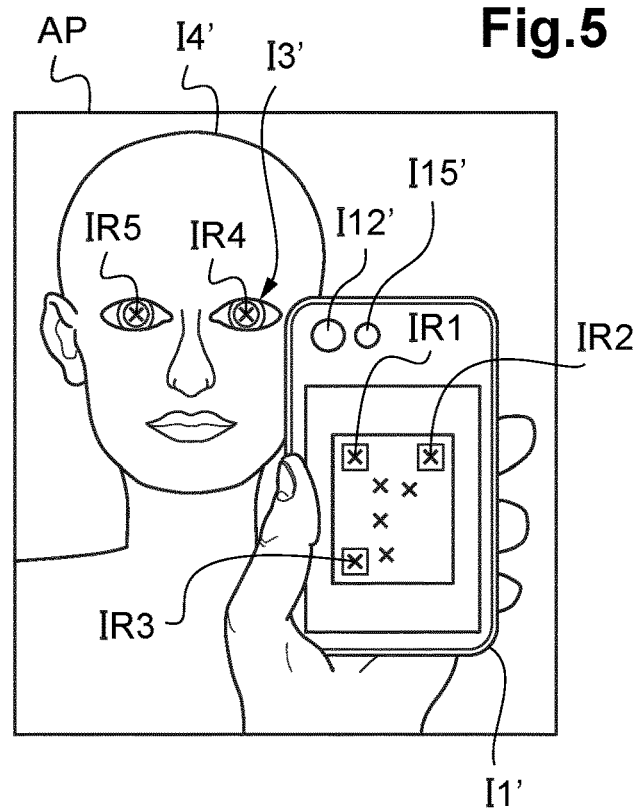
FIG. 5 is a schematic representation of a picture acquired by the image-capture apparatus of the device of FIG. 2.

Further more, in the case of the first configuration, during each execution of step b), an additional picture AP is acquired by the additional image-capture apparatus 15. Here, this additional picture AP and the picture acquired by the image-capture apparatus 10 are acquired simultaneously, at step b). The additional picture AP comprises an image 13' of the reflection 3' of the eye 3 of the subject in the mirror 7 as well as an image 11' of the reflection in the mirror of at least a part of the portable electronic device 1, which is held in front of the subject 2. As represented in FIG. 5, images I4', I12' and I15' of the reflections in the mirror 7 of at least a part of the head 4 of the subject, of the light source 12, and of the additional image-capture apparatus 15, are also present in the additional picture AP.

It is also noted, that, in the case of the second configuration (FIG. 8), the picture acquired at step b) by the image-capture apparatus comprises also, in addition to the image of the reflection 3' of the eye 3 of the subject in the mirror 7, an image of the reflection in the mirror 7 of at least a part of the portable electronic device 1.

In other embodiments, the method may comprise other sets of picture acquisitions, in addition to the three sets described above.

The method may also comprise just one of these three sets of acquisitions. So, in this case, several pictures of the eye 3 of the subject are acquired for a respective plurality of values of the eccentricity parameter e, but the orientation of the measurement plane remains constant throughout the method. Alternatively, the method may comprise just one set of successive executions of steps a) and b), during which the eccentricity parameter e remains constant, while the orientation of the measurement plane Pm is varied.

Step c) is now described in detail.

This step comprises a determination of values of the various photorefraction parameters involved in the eccentric photorefraction technique that has been described above, which comprise among others the eccentricity parameter e and the size s of the retinal reflection 31. The values are determined from the pictures acquired in step b).

Refractive features of the eye 3 of the subject are then determined from the values of these photorefraction parameters thus determined.

The determination of the values of these photorefraction parameters is described first, and the determination of the refractive features of the eye 3 in itself is presented then.

Photorefraction Parameters Determination

During step c), for each of the preceding executions of step b):
- a value of the size s and a value of the tilt angle of the retinal reflection 31 are determined by image analysis, from the picture acquired by the image-capture apparatus 10 during this execution of step b), and
- a value of the eccentricity parameter e, and the orientation of the measurement plane Pm are determined by image analysis, from the additional picture acquired by the additional image-capture apparatus 15 during the same execution of step b) (in the case of the first configuration), or from the picture acquired by the image-capture apparatus 10 during this execution of step b) (in the case of the second configuration).

The value of the size s of the retinal reflection 31 is determined for example by multiplying the dimension si of the image of this reflection 31, measured in the picture acquired by the image-capture apparatus and expressed as a number of pixels, by the conversion coefficient C determined in the calibration step So.

Regarding now the value of the eccentricity parameter e, it is determined by image analysis, from:
- the additional picture AP, acquired by the additional picture apparatus 15 during said execution of step b), when the first configuration is employed, and from
- the picture acquired by the image-capture apparatus 10 during said execution of step b), when the second configuration is employed.

This image analysis can be based on the identification, in said additional picture, or in said picture, of:
- at least two remarkable points of the eye 3, eyes 3, 6 or head 4 of the subject, and of
- at least two remarkable points of the portable electronic device 1, which is held in front of the subject.

The control unit of the portable electronic device is then programmed to determine the value of the eccentricity parameter e, and the orientation of the measurement plane with respect to the eye 3 of the subject, from the positions, in said additional picture or in said picture, of these remarkable points.

In the example of FIG. 5, the images IR4 and IR5 of the respective centers of the pupils of the eyes of the subject are identified in the additional picture AP, as well as the images IR1, IR2, IR3 of three remarkable points of a predetermined pattern displayed on the screen 11 of the portable electronic device 1. This pattern is, for example, a QR code or another kind of two-dimensional bar code.

Instead of remarkable points of a predetermined pattern displayed on this screen, the remarkable points of the portable electronic device 1 identified by image analysis could be remarkable points of the structure of the portable electronic device itself, like corners of the case of this device, for example.

The respective three-dimensional positions, in real space, of the eye 3 of the subject, and of:
- the reflection 12' of the light source in the mirror, and the image-capture apparatus 10, in the case of the first configuration, or
- the light source 12, and of the reflection 10' of the image-capture apparatus 10', in the case of the second configuration, can then be determined from the positions of the images of those remarkable points in said additional picture, or in said picture.

The value of the eccentricity parameter e, and the orientation of the measurement plane are then determined from the positions of these three elements 3, 12', 10; 3, 12, 10'.

In the case of the first configuration, the position in real space of the eye 3 of the subject can be determined as follow. First, the distance between the eye 3 of the subject and the reflection of the additional image-capture apparatus 15 in the mirror is determined from the distance (in pixels), in said additional picture AP, between the images IR4, IR5 of the two remarkable points of the eye 3, eyes 3, 6 or head 4 of the subject. This determination is carried on by scaling, similarly to the determination of the optical distance $d_{cam}$ described above. The lateral position of the eye 3, in a plane parallel to the mirror 7 is determined also from the position of the images IR4, IR5 of these two remarkable points in the additional picture. The eye 3 of the subject is thus located three-dimensionally, in real space (with respect to a reference point corresponding here to the center of the reflection of the additional image-capture apparatus 15 in the mirror).

The position and orientation of the portable electronic device 1 in real space is determined similarly. In particular, the distance between the portable electronic device 1 and its reflection in the mirror is determined by scaling, from the distance (in pixels), in said additional picture AP, between the images IR1, IR2, IR3 of said at least two remarkable points of the portable electronic device. The position of the center of the entrance pupil 100 of the image-capture apparatus 10 in space is then determined, from the position and orientation of the portable electronic device in which it is embedded.

Regarding the position of the reflection 12' of the light source in the mirror, it is close to the position of the reflection of the additional image-capture apparatus 15 in the mirror, with respect to which the eye 3 and the image-capture apparatus 10 have been located. Anyhow, the position of the reflection 12' of the light source in the mirror can also be precisely determined from the positions of the remarkable points of the portable electronic device identified in the additional picture.

Alternatively, the value of the eccentricity parameter e can be determined from the first or from the second offset angle $\gamma_1$, $\gamma_2$, instead of being determined from three-dimensional positions of the eye, image-capture apparatus, and reflection of the light source. In such a case, the distance $d_{12\text{-}12'}$ between the light source 12 and its reflection 12' in the mirror 7 is first determined by scaling, from the distance (in pixels), in said additional picture AP, between the images IR1, IR2, IR3 of said at least two remarkable points of the portable electronic device. The distance $d_{3\text{-}12'}$ between the eye 3 of the subject and the reflection 12' of the light source in the mirror 7 is also determined by scaling, from the distance (in pixels), in said additional picture AP, between the images IR4, IR5 of the two remarkable points of the eye 3, eyes 3, 6 or head 4 of the subject. The value of the first, or of the second offset angle $\gamma_1$, $\gamma_2$ is then determined from those two distances $d_{12\text{-}12'}$, $d_{3\text{-}12'}$ and from the distance $d_{cam}$ between the eye 3 and the image-capture apparatus 10, using Al-Kashi formula:

$$\gamma_{1,2} = \arccos([d_{cam}^2 + d_{3\text{-}12'}^2 - d_{12\text{-}12'}^2]/[2 \cdot d_{cam} \cdot d_{12\text{-}12'}])$$

The value of the eccentricity parameter e is then determined from the value of the first, or of the second offset angle $\gamma_1$, $\gamma_2$.

In the case of the second configuration, the value of the eccentricity parameter e and the orientation of the measurement plane can be achieved similarly, while considering the light source 12 and of the reflection 10' of the image-capture apparatus 10', instead of considering the reflection 12' of the light source in the mirror and the image-capture apparatus 10.

The value of the diameter ϕ of the pupil 30 of the eye is also determined, by image analysis, from one or several of the pictures acquired at step b).

Concerning the optical distance $d_{cam}$ between the pupil 30 of the eye 3 and the entrance pupil 100 of the image-capture apparatus 10, it has already been determined during the initial calibration step So, in the exemplary embodiment described here.

Refractive Features Determination

Refractive features of the eye 3, comprising here the spherical power and the cylindrical power of the refraction error of the eye 3, and the orientation of the axis of the corresponding cylinder, are then determined from:
- the values of the size s and of the tilt angle of the retinal reflection 31, and
- the corresponding value of the eccentricity parameter e and the orientation of the measurement plane, determined for each execution of step b), and from:
- the value of the diameter ϕ of the pupil 30, and
- the value of the optical distance $d_{cam}$ between the pupil 30 of the eye 3 and the entrance pupil 100 of the image-capture apparatus 10 previously determined.

Taking into account these sets of values of the size s of the retinal reflection 31, each corresponding to a different value of the eccentricity parameter e, improves the accuracy of the refractive features thus determined, compared to a case in which the eccentricity parameter would remain the same for all the pictures acquired. These refractive features can be determined, for example, by a curve fitting process, taking this set of values of the size s, and the corresponding values of the eccentricity parameter e as input data.

And taking into account several values of the size s and tilt of the retinal reflection 31, each corresponding to a different orientation of the measurement plane enables to determine the astigmatism features of the eye, as already explained.

If the pictures acquired at step b) were acquired while the subject 2 was wearing a corrective ophthalmic lens in front of his eye 3, or in contact with his eye 3, then the refractive feature or features of this lens are taken into account while determining the refractive features of his eye 3. For example, if a contact lens is present on the eye 3 of the subject, the spherical power of this lens is added to a raw spherical power, which is determined from the size s of the corneal reflection 31 while ignoring the presence of this contact lens.

Further, if the subject 2 was invited to look at an element located at a finite distance from his eye 3, this distance is taken into account to determine the refractive features of his eye 3, considering that his eye 3 is was focused on that element during the picture acquisition of step b). For instance, if the subject was invited at step S'o to look at the reflection 3' of his eye in the mirror 7, this reflection 3' being located 1 meter ahead of his eye 3, and if the spherical power determined from the size s of the retinal reflection is equal to −2 diopters, then, the value of spherical power finally determined and delivered by the portable electronic device 1 is equal to −3 diopters.

The portable electronic device 1 could also be programmed so that, when the subject 2 is invited, at step S'o, to look at a visual target located several meters ahead from him, then, said refractive features is determined while taking into account that the eye 3 of the subject was focused on a point located as far as possible to the subject (in view of the ametropia of this eye) during the acquisitions of said pictures. In this case, the above-mentioned corrections may be omitted.

In addition to the steps described above, the method may also comprise a step of transmitting the refraction features of the eye 3 of the subject 2, determined in step c), to a remote data server, by means of the communication module of the portable electronic device 1.

The method may also comprise a step of proposing to order an optical equipment from a remote online supplier, the features of this optical equipment being preselected automatically (that is, without requesting an action from the subject 2) on the basis of refraction features determined in step c). These features may comprise the spherical and/or cylindrical power of the corrective ophthalmic lens or lenses of this optical equipment. During this step, this optical equipment is ordered by means of the communication module of the portable electronic device 1.

The method may also comprise a group of steps that enables to check that the lighting conditions in the environment of the subject are adequate to determine the refractive features of the eye 3 of the subject 2, in particular that an ambient light intensity is small enough. More specifically, the method may comprise the steps of:
- measuring the ambient light intensity $I_A$,
- comparing the ambient light intensity $I_A$ that has been measured to a predetermined threshold, and
- if the ambient light intensity $I_A$ is above said threshold, determining that the determination of refractive features or feature of the eye 3 of the subject is feasible and/or reliable, or, on the contrary,
- if the ambient light intensity $I_A$ is below said threshold, determining that that the determination of these refractive features or feature is not feasible or reliable, and that the ambient light intensity $I_A$ should be reduced, and then instructing the subject to reduce the ambient light intensity.

This predetermined threshold may be equal to the value of said lighting conditions parameter in a threshold situation in which the intensity of the ambient light incident on the subject's face is equal to 1000 candelas per square meter, or equal to 300 candelas per square meter, or even to 50 candelas per square meter.

Checking the lighting conditions in the environment of the subject is advantageous, as the method is implanted here with a general purpose smartphone or computer tablet whose light source is generally less bright than the one of a conventional retinoscope.

The determination of one or more refraction features of one of the eyes 3, 6 of the subject 2 (as represented in the figures, its left eye 3) has been described above. However, the method may comprise the determination of one or more refraction features of each of the two eyes 3, 6 of the subject 2.

The invention claimed is:

1. A method for determining a refraction feature of an eye of a subject using a light source and an image-capture apparatus, said method comprising the steps of :
   a) illuminating a pupil of the eye of the subject by means of said light source;
   b) acquiring at least one picture of said pupil of the eye of the subject comprising an image of the reflection of said light source on the retina of said eye of the subject;

c) determining said refraction feature of said eye of the subject from at least one of the following features of said image of the reflection of said light source:
   a geometrical feature of said image of the reflection of said light source,
   a positional feature of said image of the reflection of said light source,
   an intensity distribution within said image of the reflection of said light source, wherein,
said light source and said image-capture apparatus are positioned respectively in an illumination plane and in an image-capture plane that are different from each other, and wherein an absolute value of a difference between:
an optical distance between said light source and the pupil of the eye of the subject, and
an optical distance between said image-capture apparatus and said pupil,
is higher than 0.2 meter.

2. The method according to claim 1 wherein said light source and image-capture apparatus belonging to a portable electronic device, and being oriented in opposite directions, in step b), the subject faces a mirror and the portable electronic device is placed between said subject and said mirror, in such a way that said picture of the pupil of the eye of the subject is:
   a picture of the eye of the subject acquired without reflection on said mirror, while said is pupil illuminated by a reflection of the light source in the mirror; or
   a picture of a reflection of the eye of the subject in the mirror, while said pupil is illuminated directly by the light source.

3. The method according to claim 2, wherein, in step b), the subject looks straight ahead in the distance.

4. The method according to claim 2, wherein said light source of the portable electronic device is shifted from the axis that links the pupil of the eye of the subject and the image of this pupil in the mirror.

5. The method according to claim 2, wherein, in step b), the subject directs his gaze towards one of the following: an entrance pupil of said image-capture apparatus, a reflection of the entrance pupil of said image-capture apparatus in the mirror, said light source, the reflection of said light source in the mirror, the reflection of one of his own eyes, his own reflection.

6. The method according to claim 2, wherein steps a) and b) are repeated in order to acquire a plurality of pictures of said pupil of the eye of the subject comprising an image of the reflection of said light source on the retina of said eye of the subject, the posture of the head of the subject relative to said light source or said reflection of the light source in the mirror being different while each of said pictures are acquired.

7. The method according to claim 6, wherein, between the acquisitions of two different pictures of said pupil of the eye of the subject:
   a first offset angle between a first illumination axis linking the reflection of the light source in the mirror and the eye of the subject and a first observation axis linking the image-capture apparatus and the eye of the subject, or
   a second offset angle between a second illumination axis linking the light source and the eye of the subject and a second observation axis linking the reflection of the image capture apparatus in the mirror and the eye of the subject,
is modified.

8. The method according to claim 6, wherein, during the acquisition of said plurality of pictures, the subject moves his head relative to the light source or relative to said reflection of the light source in the mirror while keeping the optical distance between the image-capture apparatus and the pupil of the eye constant.

9. The method according to claim 2, wherein, in step a), said light source illuminates the pupil of the eye by a flash of light and the image-capture apparatus is synchronized to acquire said picture of the pupil of the eye of the subject simultaneously, while the eye is illuminated by this flash of light.

10. The method according to claim 2, wherein in step b) the subject wears a corrective ophthalmic lens in front of his eye and in step c), the optical features of this corrective ophthalmic lens is taken into account for determining the refraction feature of the eye.

11. The method according to claim 2, wherein,
   the distance between the image-capture apparatus and the pupil of the eye of the subject and/or the distance between the reflection of the light source in the mirror and the pupil of the eye of the subject, or
   the distance between the reflection of the image-capture apparatus in the mirror and the pupil of the eye of the subject and/or the distance between the light source and the pupil of the eye of the subject,
   are determined.

12. The method according to claim 11, wherein the distance between pupil of the eye of the subject and
   the image-capture apparatus, or
   the reflection of the image-capture apparatus in the mirror,
   is determined taking into account a distance between two remarkable points of the head of the subject identified on a picture acquired by said image-capture apparatus, or taking into account an image of a predetermined object held close of the head of the subject, identified on a picture acquired by said image-capture apparatus.

13. The method according to claim 11, wherein the distance between the pupil of the eye of the subject and:
   the reflection of the light source, or
   the light source,
   is determined by identifying, on a picture acquired by said image-capture apparatus, or by an additional image-capture apparatus oriented in the same direction as the light-source, the images of two remarkable points of the portable electronic device.

14. The method according to claim 2, wherein, in step c), said refraction feature is determined on the basis of an eccentricity parameter which is representative of a side shift between:
   the reflection of the light source in the mirror and the image-capture apparatus, or between
   the light source and the reflection of the image-capture apparatus in the mirror, and
   wherein a value of the eccentricity parameter is determined by image analysis:
   from an additional picture acquired at step b) by an additional image-capture apparatus oriented in the same direction as the light-source, said additional picture comprising an image of the reflection of the eye of the subject in the mirror and an image of the reflection of the portable electronic device in the mirror, or
   from the picture acquired by the image-capture apparatus at step b), said picture further comprising an image of the reflection of the portable electronic device in the mirror.

15. A device for determining a refraction feature of an eye of a subject, the device comprising a light source and an image-capture apparatus, and being configured to execute the steps of:
- a) illuminating a pupil of the eye of the subject by means of said light source;
- b) acquiring at least one picture of said pupil of the eye of the subject comprising an image of the reflection of said light source on the retina of said eye of the subject, by means of said image-capture apparatus;
- c) determining said refraction feature of said eye of the subject from at least one of the following features of said image of the reflection of said light source:
    - a geometrical feature of said image of the reflection of said light source,
    - a positional feature of said image of the reflection of said light source,
    - an intensity distribution within said image of the reflection of said light source;

wherein said light source and said image-capture apparatus are positioned respectively in an illumination plane and in an image-capture plane that are different from each other, and wherein an absolute value of a difference between:

an optical distance between said light source and the pupil of the eye of the subject, and an optical distance between said image-capture apparatus and said pupil, is higher than 0.2 meter.

16. The method according to claim 3, wherein said light source of the portable electronic device is shifted from the axis that links the pupil of the eye of the subject and the image of this pupil in the mirror.

17. The method according to claim 3, wherein, in step b), the subject directs his gaze towards one of the following: an entrance pupil of said image-capture apparatus, a reflection of the entrance pupil of said image-capture apparatus in the mirror, said light source, the reflection of said light source in the mirror, the reflection of one of his own eyes, his own reflection.

18. The method according to claim 4, wherein, in step b), the subject directs his gaze towards one of the following: an entrance pupil of said image-capture apparatus, a reflection of the entrance pupil of said image-capture apparatus in the mirror, said light source, the reflection of said light source in the mirror, the reflection of one of his own eyes, his own reflection.

19. The method according to claim 3, wherein steps a) and b) are repeated in order to acquire a plurality of pictures of said pupil of the eye of the subject comprising an image of the reflection of said light source on the retina of said eye of the subject, the posture of the head of the subject relative to said light source or said reflection of the light source in the mirror being different while each of said pictures are acquired.

20. The method according to claim 4, wherein steps a) and b) are repeated in order to acquire a plurality of pictures of said pupil of the eye of the subject comprising an image of the reflection of said light source on the retina of said eye of the subject, the posture of the head of the subject relative to said light source or said reflection of the light source in the mirror being different while each of said pictures are acquired.

* * * * *